US008593278B2

(12) United States Patent
Churbock et al.

(10) Patent No.: US 8,593,278 B2
(45) Date of Patent: Nov. 26, 2013

(54) MEDICATION STORAGE DEVICE USAGE STATUS NOTIFICATIONS

(75) Inventors: Preeti Churbock, Pittsburgh, PA (US); Emilie Ray, Cranberry, PA (US)

(73) Assignee: McKesson Automation Inc., Cranberry, PA (US)

( * ) Notice: Subject to any disclaimer, the term of this patent is extended or adjusted under 35 U.S.C. 154(b) by 421 days.

(21) Appl. No.: 12/749,272

(22) Filed: Mar. 29, 2010

(65) Prior Publication Data

US 2011/0234419 A1 Sep. 29, 2011

(51) Int. Cl.
G08B 1/08 (2006.01)

(52) U.S. Cl.
USPC .............. 340/539.29; 128/204.18; 128/903; 340/286.07; 340/539.12; 600/300; 700/231; 700/242; 705/2

(58) Field of Classification Search
USPC .............. 340/539.29, 539.12, 5.81, 309.16, 340/286.07, 10.1, 691.1, 500, 573.1; 600/300; 128/897, 903, 204.18, 128/202.27; 705/2, 3, 500; 700/231, 239, 700/242, 244, 236
See application file for complete search history.

(56) References Cited

U.S. PATENT DOCUMENTS

| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |

(Continued)

Primary Examiner — Brent Swarthout
(74) Attorney, Agent, or Firm — Alston & Bird LLP (57) ABSTRACT

A usage status notification method and corresponding medication storage device (e.g., mobile medication dispensing cart, medication cabinet, nurse server, etc.) are provided. To generate the usage status notification, the status of one or more components of the medication storage device may be monitored. An in-use notification signal may be generated if it is determined that the medication storage device is in use at a certain point in time (e.g., when a user is logged into the medication storage device). An available notification signal may be generated if it is determined that the medication storage device is available for use at a certain point in time (e.g., when a user is logged out of the medication storage device). Other types of usage status signals may also be provided.

21 Claims, 6 Drawing Sheets

(56) References Cited

U.S. PATENT DOCUMENTS

| | | |
|---|---|---|
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,175,779 B1 * | 1/2001 | Barrett ............ 700/242 |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,289,656 B1 | 9/2001 | Wangu et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,609,047 B1 | 8/2003 | Lipps |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 7,654,261 B1 * | 2/2010 | Rockhold ............ 128/204.18 |
| 2002/0017599 A1 * | 2/2002 | Shimizu ............ 250/208.1 |
| 2002/0130904 A1 * | 9/2002 | Becker et al. ............ 345/753 |
| 2004/0054436 A1 * | 3/2004 | Haitin et al. ............ 700/236 |
| 2006/0079994 A1 * | 4/2006 | Chu et al. ............ 700/231 |
| 2008/0201474 A1 * | 8/2008 | Yamada ............ 709/226 |
| 2009/0194987 A1 | 8/2009 | Christie et al. |
| 2009/0210089 A1 * | 8/2009 | Christie et al. ............ 700/244 |
| 2009/0267772 A1 * | 10/2009 | Dehnadi ............ 340/572.8 |
| 2010/0004780 A1 * | 1/2010 | Rickelhoff ............ 700/231 |
| 2010/0004782 A1 * | 1/2010 | Siegel et al. ............ 700/242 |

* cited by examiner

MEDICATION STORAGE DEVICE USAGE STATUS NOTIFICATIONS

FIELD

Embodiments of the invention relate, generally, to medication storage devices and, in particular, to a technique for indicating the usage status of anesthesia and other medication storage devices.

BACKGROUND

One way for doctors, anesthesiologists, nurses, pharmacists, technicians, and the like (referred to hereinafter as "healthcare workers") to store, transport and dispense medications to their patients is through the use of medication storage devices (e.g., a mobile medication dispensing cart, a medication cabinet, a nurse server, etc.). In particular, a number of healthcare workers may share a couple of medication storage devices, which store various medications and/or items used for dispensing or delivering those medications (e.g., syringes, gloves, etc.). An example of such a medication storage device may be an anesthesia cart used by an anesthesiologist for storing all of the medications and dispensing/delivery equipment needed for the procedures (e.g., surgeries) that are planned for a given period of time (e.g., one workday).

In many instances medication storage devices may include controlled substances including, for example, various types of narcotics. Some medication storage devices can be mobile and moved among hospital or other types of rooms, and used to administer the narcotics and/or other supplies. After the medical procedure is complete, the mobile cart is usually returned to a central location, so another healthcare provider can use it.

Currently, it is hard for healthcare workers and information technology service providers to determine whether a medication storage device is in use or not, where medication storage devices are currently located, and also whether the medication storage devices are working properly or not. Embodiments of the present invention overcome, among other things, many of the drawbacks faced by healthcare workers and information technology service providers that use and maintain medication storage devices.

BRIEF SUMMARY

In general, embodiments of the present invention provide improvements by, among other things, providing a usage status notification procedure and system whereby the status of a medication storage device can be communicated to potential users. For example, the medication storage device can include a processor and a usage indicator (such as, e.g., one or more lights mounted on a post or other support member). The processor can be configured to control the usage indicator and, in some embodiments, communicate via a network with one or more remote devices.

Among other things, the medication storage device can be configured to determine its usage status. Exemplary types of usage statuses may include an in-use status, an available for use status, a status indicative of a technical error status, or a status indicative of a need for supplies. (As used herein "supplies" refer to medications, disposable tools, dispensing equipment, or anything else that may need to be replenished within the medication storage device.) While some embodiments provide separate usage indicators for each type of usage status, one or a combination of usage indicators can be used to broadly represent a more generic usage status of the medication storage device. For example, the in-use status indicator (e.g., a red light) can be used to broadly represent that the medication storage device is generally unavailable for use (that it is, e.g., in-use, in need of supplies, and/or experiencing a technical error).

The processor of the medication storage device can be configured to generate a usage status signal that corresponds with the usage status of the medication storage device. For example, the processor can be configured to generate an in-use notification signal, available notification signal, supply notification signal, and/or error notification signal. The usage status signal can then be sent to one or more usage indicators. The medication storage device may include local usage indicators. Additionally or alternatively, the medication device may be configured to communicate a usage status signal to a networked or other remote usage indicator. For example, a central posting board can be used to indicate the usage status of a plurality of medication storage devices.

In some embodiments, a determination can be made that a medication storage device is being used in response to a user logging into an application running on the medication storage device. In addition or instead of using user entered information, a determination can be made that a medication storage device is in use based on the utilization and/or accessing of a component of the medication storage device. The determination can be made by the medication storage device and/or by another device, such as a central, network device. Similarly, a determination can be made that the medication storage device is available for use in response to the user logging out of the application or no longer using the component(s) of the medication storage device.

Should a technical error occur with a medication storage device, the device may assume a technical error status. Error information, including an error notification signal, time information related to when the device entered error status, location information, and any other information can be stored and/or provided to another device, such as a central, networked device. Information technology service providers or others can then use the error information to locate the medication storage device and addresses the technical error.

Similarly, a pharmacist may be notified when a medication storage device is low on supplies. For example, in response to determining that one or more supplies have been depleted below a predetermined threshold level, a usage notification signal can be generated by the medication storage device and provided to local/remote usage indicators. The pharmacist may then be able to quickly identify which of the medication storage devices is in need of what supplies, without having to telephone other healthcare workers or search through the hospital for the medication storage device. Similarly, the pharmacist may be informed as to when it would be a good time to supply the medication storage device (e.g., such as when the medication storage device is available). In some embodiments, an available notification signal can be used to notify the pharmacist as to when it would be a good time to supply the medication storage device. In addition to or instead of an available notification signal generated by the medication storage device, a scheduling or other type of system can be used to determine when it would be a good time to supply the medication storage device. For example, it may be a good time to supply the medication storage device after the medication storage device completes a pre-scheduled procedure or set of procedures. This information can then be provided to the pharmacist, coupled with a supply notification signal, indicating the best time or times to replenish the supplies of a medication storage device.

BRIEF DESCRIPTION OF THE SEVERAL VIEWS OF THE DRAWING(S)

Having thus described embodiments of the invention in general terms, reference will now be made to the accompanying drawings, which are not necessarily drawn to scale, and wherein:

DETAILED DESCRIPTION

Embodiments of the present invention now will be described more fully hereinafter with reference to the accompanying drawings, in which some, but not all embodiments of the inventions are shown. Indeed, embodiments of the invention may be embodied in many different forms and should not be construed as limited to the embodiments set forth herein; rather, these embodiments are provided so that this disclosure will satisfy applicable legal requirements. Like numbers refer to like elements throughout.

In general, embodiments of the present invention include medication storage devices (e.g., mobile medication dispensing carts, medication cabinets, nurse servers, etc.), and associated methods for generating and/or providing usage status signals. Usage status signals can be used to provide usage status notifications that relating to a medical storage device indicate, e.g., whether a medication storage device is being used or available for use. For example, usage status notifications can assist healthcare workers, pharmacists, service personnel, and others by allowing them to see from a distance and/or at a remote location whether one or more medication storage devices are currently being used. In this manner, healthcare workers would not have to walk around or make telephone calls to locate and determine whether a medical storage device is currently being used.

Figure 1:
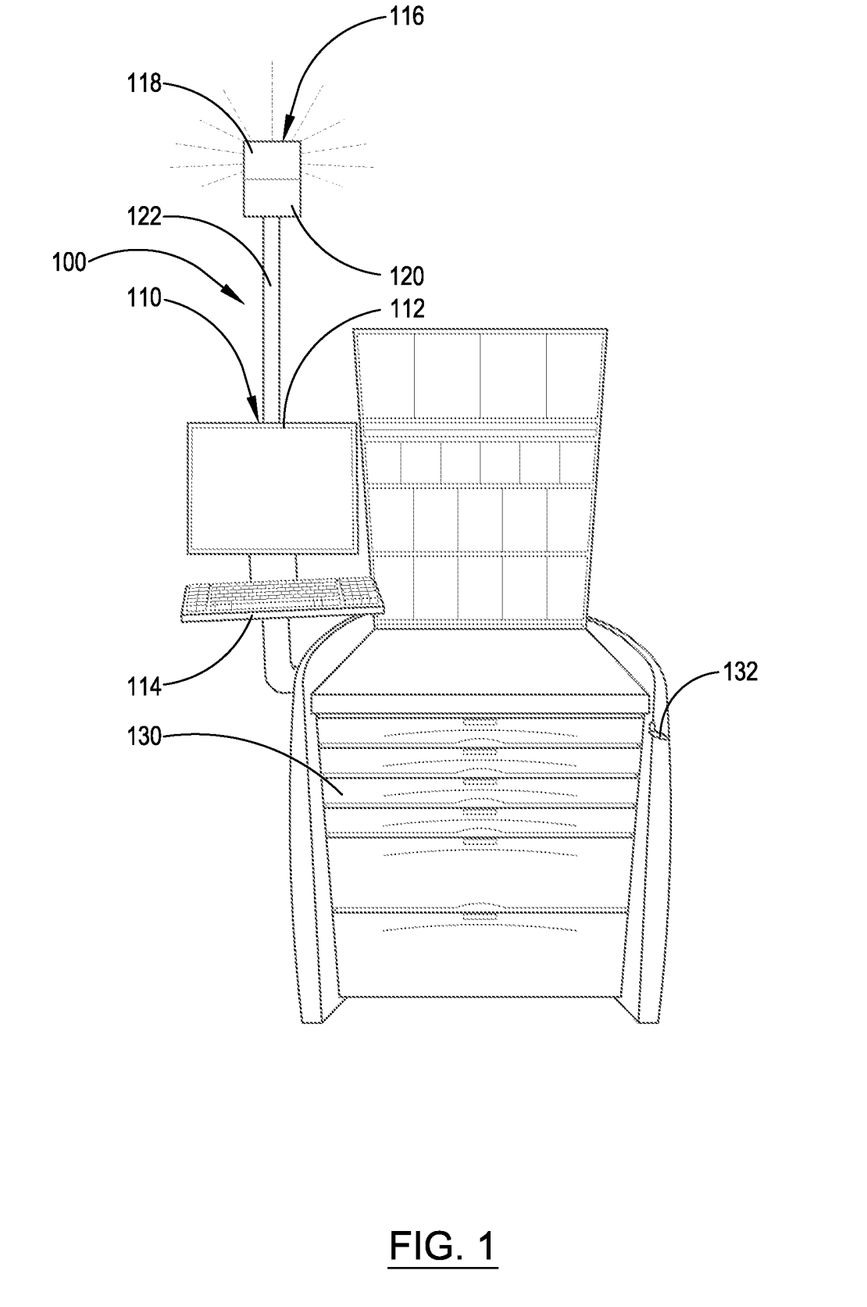
FIG. 1 shows a mobile medication dispensing cart in accordance with some embodiments.

Reference is now made to FIG. 1, which provides an example of one type of medication storage device that may be used in conjunction with embodiments of the present invention. FIG. 1 shows an exemplary medication storage device that is a mobile medication dispensing cart, namely medication cart 100. Medication cart 100 may be, for example, an AcuDose-Rx® medication dispensing cabinet that combines configurable drawer options, biometrics, advanced reporting capabilities and network integration for security, patient safety, efficiency and cost savings. As one of ordinary skill in the art will recognize, other types of medication storage devices, including, but not limited to, a stationary (e.g., wall-mounted) medication cabinet, a nurse server, and/or various other types of medication storage equipment or devices, such as McKesson's CarePoint-RN® line of mobile medication cabinets, may benefit from embodiments discussed herein. Accordingly, while embodiments herein describe the usage status notifications, both local to and remote from medication cart 100, embodiments of the present invention are exemplary and not so limited.

As shown in FIG. 1, medication cart 100 may include computing device 110 (e.g., desktop computer, laptop computer, tablet, or any other type of computing device), which is discussed in more detail below with regard to FIG. 2. For example, computing device can be configured to implement McKesson's Anesthesia-RX™ solution, which is designed to complement complex operating room workflow, while guaranteeing that anesthesiologists, nurses, and other healthcare workers have access to the medications when needed. Computing device 100 can be used to access information associated with the medications, and dispensing/delivery devices and other supplies stored in the medication cart, as well as information associated with the patients for whom medications may be dispensed from the medication cart at a given point in time. In some embodiments, some or all of this information may be stored locally in memory associated with computing device 110. For example, information associated with the medications and dispensing/delivery devices stored in the medication cart and their location within the medication cart, may be input into computing device 110 at or near the time when the medication cart is first put into use and automatically updated thereafter as medications are added and/or dispensed. Alternatively, or in addition, some or all of the information may be accessed by computing device 110, for example via a wireless communication network, on a central server or system, which are discussed in more detail below with regard to FIG. 3, associated with the healthcare facility in which the medication cart is being used.

Computing device 110 can also be configured to request information regarding a patient, as well as input information regarding the medications he or she is dispensing. Accordingly, the computing device 110 may include a display screen 112, a keyboard 114, and/or other input and/or output devices, which are not shown and which may include, for example, a speaker, a barcode reader, a radio frequency identification (RFID) tag reader, a biometric scanner, touch-sensitive screen, among other types of components that can receive user identifying information.

Before a user can use computing device 110 to perform one or more actions, such as accessing a patient's information or dispensing medication, computing device 110 may require a healthcare worker or other type of user (e.g., information technology, service provider, etc.) to enter login or other user identifying information. For example, a user may be required to type a username and password using keyboard 114, use a key to manually release a lock, submit to a biometric scan, place a RFID card up to a reader, and/or perform any other action that enables computing device 110 to identify the user and authorize the user's access to medication cart 100. In some embodiments, computing device 110 can locally process the entered user identifying information and authorize the user's access to computing device 110. Alternatively, or in addition, the authentication and authorization of a user may involve accessing and/or communicating with a remotely located, network device.

Upon authorizing the user's access to medication cart 100, computing device 110 can be configured to generate an in-use notification signal. As referenced herein, the in-use notification signal is a type of usage status signal that can be sent to a component of medication cart 100 and/or a network device. For example, the in-use notification signal can be sent locally to display 112 and/or usage indicator 116. Usage indicator 116 is shown in FIG. 1 as being adapted to be seen from a distance if there is a line of sight to usage indicator 116. For example, a healthcare worker may be able to look down a hospital hallway at usage indicator 116 and quickly determine whether or not medication cart 100 is currently being used.

Usage indicator 116 can also include at least one lighting device. In FIG. 1, usage indicator 116 includes two lighting devices, namely light 118 and light 120. Light 118 and light 120 can be different colors (e.g., red and green, respectively) and/or include other distinguishing attribute(s) (e.g., shape, illumination, pulse rate, etc.) that indicate the usage status of medication care 100. Light 118 can be illuminated, for example, in response to receiving an in-use notification signal, while light 120 can be illuminated in response to receiving an available notification signal. The in-use notification signal, available notification signal and/or other type of usage status signal can be generated by computing device 110 or other component of medication device 100. Light 118 and/or light 120 may also be illuminated in response to receiving a usage status signal or other type of signal from a remotely located device (discussed below in connection with FIG. 3). In some embodiments, usage indicator 116 can be configured such that light 120 is adapted to be illuminated any time light 118 is not (or vice-versa). Since the status conditions indicated by the two lights are mutually exclusive and one of the status conditions is always in effect. Display screen 112 can also present usage status information for medication cart 100 and/or one or more other medication storage devices, wherein the usage status information is based on usage status signals generated locally at computing device 112 or remotely by another device (such as those discussed in reference to FIG. 3).

Although usage indicator 116 is shown as including two lighting devices, one skilled in the art would appreciate that any number of lighting devices can be included as a usage indicator. For example, usage indicator can include four lighting devices, wherein each lighting device is dedicated to a different type of usage status notification (namely, in-use, available for use, experiencing a technical error, and low on supplies). Similarly, one skilled in the art would appreciate that multiple types of usage status notifications may be associated with a single portion of usage indicator 116 (e.g., the medication storage device is available, stocked, and functioning properly if the light 120 is ON, but is in-use, not functioning properly or low on supplies if light 120 is OFF). In addition to or instead light-based usage indicators, other types of usage indicators may be employed, such as audible indicators.

The usage status signals can each be any type of signal. For example, the in-use notification signal can be a signal that provides power (such as e.g., a 5V direct current signal) to a usage indicator, such as usage indicator 116. As another example, the in-use notification signal can comprise one or more instructions that cause another component to provide power to a user indicator or other type of user interface. Alternatively, or in addition, the in-use notification signal can also include data such as, for example, user identifying data, device identifying data (including name, type, etc. of medication cart 100), location data identifying the location of medication cart 100, error data (including when medication cart 100 entered a fault mode), medication and/or supply data (including types and remaining quantities), and/or any other data that may be generated or received by medication cart 100.

The in-use notification signal can be generated in response to, for example, a user signing into computing device 110. As another example, the in-use notification signal can be generated in response to a user accessing a component of medication cart 100. For example, a user may select a dedicated button included in medication cart 100, access one or more drawers 130, unlock a mechanical lock and/or cause any other manual, electrical or electro-mechanical triggering event. In some embodiments, the in-use notification signal can be generated when medication cart 100 is unable to operate (do to, e.g., a technical error). In other embodiments, a separate type of usage status signal, such as an error notification signal, can be generated when medication cart 100 is unable to operate as intended.

The medication cart 100 may further include one or more drawers 130 for storing the various medications and dispensing/delivery devices, as well as a manual, keyless lock 132 for locking and unlocking drawers 130 of medication cart 100. In the embodiment shown in FIG. 1, a single lock, which may include, for example, a lever, may be used to lock and unlock all of drawers 130 of medication cart 100 together. In particular, according to this embodiment, all drawers 130 of medication cart 100 may be capable of being opened when lock 132 is unlocked, while none of drawers 130 may be capable of being opened when lock 132 is locked. In another embodiment, separate locks may be used for each of drawers 130, wherein each drawer is locked and unlocked individually. In addition, while not shown, other types of manual, keyless or keyed locks may likewise be used without departing from the spirit and scope of some embodiments. For example, some embodiments may include the use of a biometric lock (e.g., using fingerprint recognition), a secure identification code-based lock, and/or any other type of lock.

While not shown, according to some embodiments, the medication cart 100 may further include one or more electronic sensors associated with one or more drawers 130, lock 132, and/or any other component of medication cart 100. The electronic sensors can be used to generate one or more signals that may be or be used to derive a usage status signal. For example, an electronic sensor can be in electrical communication with computing device 110 and/or usage indicator 116, and be configured to monitor the usage status of one or more components of medication cart 100. A signal representing the component's usage status can then be provided to computing device 110 for use in generating usage status signals for medication cart 100. In some embodiments, if any one of medication cart 100's sensors detects that medication cart 100 is in-use, such as due to a drawer opening, the unlocking of a lock or other predefined activity that causes the generation of a component usage signal, an in-use notification signal can be generated; otherwise an available notification signal can be generated (even, in some embodiments, if the user is logged in). Usage signals generated by components of a medication storage device are sometimes referred to herein as "component usage signals." In other embodiments, computing device 110 may be configured to only generate an in-use modification signal (or other type of usage status signal) in response to receiving a number of usage signals generated by one or more components of medication cart 100. In yet other embodiments, a hybrid approach may be employed, wherein computing device 110 analyzes each component usage signal to determine whether or not a cart usage notification signal should be generated based on, e.g., received user identifying information (e.g., whether or not a user is logged into an application and/or which application(s) being run by computing device 110).

Each of the sensors may be configured to provide a digital and/or analog output. One or more of the sensors may be comprised of, for example, a position sensor, contact sensor, optical sensor, proximity sensor, magnetic switch, any other type of sensor, or any combination thereof that is configured to determine usage information for one or more components of medication cart 100, such as one or more of drawers 130 and lock 132. For example, one or more electronic sensors associated with one of drawers 130 may be configured to monitor whether the drawer is locked, unlocked, opened and/or closed and then likewise communicate this information as a component usage signal to the computing device 110. As another example, an electronic sensor associated with lock 132 may be configured to monitor whether lock 132 is locked or unlocked and then, based on this information, communicate a component usage signal to computing device 110 for generating one or more usage status notifications.

Figure 2:
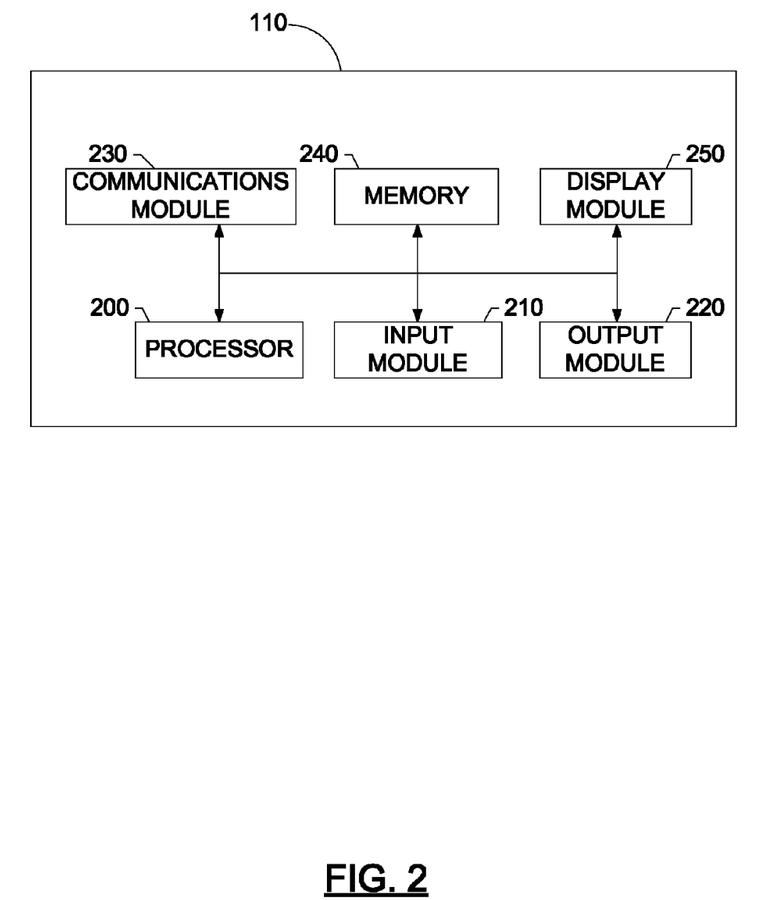
FIG. 2 is a schematic block diagram of a computing device of a medication storage device, such as the medication cart, in accordance with some embodiments.

Referring now to FIG. 2, a block diagram is provided of an entity capable of operating as computing device 110 associated with a medication storage device, such as medication cart 100 or other type of medication storage device. The entity capable of operating as computing device 110 may include various means for performing one or more functions in accordance with some embodiments, including those more particularly shown and described herein. It should be understood, however, that one or more of the entities may include alternative means for performing one or more like functions, without departing from the spirit and scope of embodiments discussed herein. As shown, the entity capable of operating as computing device 110 can generally include means, such as processor 200 for performing or controlling the various functions of the entity.

Processor 200 may be configured to receive a signal from input module 210, which may include specialized circuitry, one or more ports (serial, such as universal serial bus "USB" ports, and/or parallel ports), and/or any other component that facilitates the reception of signals from an input component. In some embodiments, input module 210 can function as a user input interface and, in turn, receive data from any of a number and/or types of devices and/or users. For example, input module 210 may be electrically coupled to a sensor, such as, e.g., a lock sensor, drawer sensor, and/or other sensor included in medication cart 100. As another example, processor 200 may also receive user entered information via input module 210 generated by a user-input device, such as, e.g., keyboard 114, a RFID reader, a barcode reader, a dedicated in-use button (e.g., a switch that can be manually toggled to indicate medication cart 100 is in-use, available and/or in need of servicing), touch device, joystick, and/or any other device that can be used to receive user inputs (including, e.g., receive user identifying information). Although more than one input modules, can be included in computing device 110, only one is shown in FIG. 2 to avoid overcomplicating the drawing (like the other components discussed herein).

In this regard, input module 210 can provide one or more input signals including user identifying information and/or component usage signals, to processor 200 that indicates whether one or more components of medication cart 100 is being used or is available for use. In this regard, processor 200 may be configured to use the received signal(s) to determine whether medication cart 100 is being used. In some embodiments, being available for use includes being available to, e.g., dispense medication, be moved to a different area of a hospital, be repaired or updated by a service worker, be restocked with supplies, and/or perform any other action that may not be performed while medication cart 100 is being used. In other embodiments, being available for use only refers to whether or not the medication storage device is being used and is independent from other potential usage status notifications (e.g., in need of supplies, experiencing a technical error, etc.). For example, a determination can be made that the system is available for use if a user is not logged into an application running on computing device 110.

As noted above, in response to determining medication cart 100 is in-use, processor 200 can be configured to generate an in-use notification signal that causes a user interface to indicate medication cart 100 is currently being used. For example, the in-use notification signal can be generated by processor 200 in response to authenticated user identifying information being received. The in-use notification signal can then facilitate the providing of power to a local user interface via output module 220. In this regard, output module 220 can receive the in-use notification signal from processor 200 and, in response, provide power to a lighting device (such as, e.g., light 118 of usage indicator 116), thereby causing the lighting device to illuminate.

In some embodiments, the in-use notification signal can also cause an availability indicator to be disabled (e.g., turned OFF). For example, usage indicator 116 can be adapted to indicate when medication cart 100 is available (using, e.g., light 120 of usage indicator 116) and, in response to receiving the in-use notification signal, output module 220 can be configured to stop powering light 120 of usage indicator 116 (even if another portion, namely light 118, receives power).

Some embodiments of processor 200 can also be configured to generate an available notification signal that causes another type of user interface to indicate medication cart 100 is currently available for use. The available notification signal can be generated in response to, for example, processor 200 determining a user has logged OFF of an application associated with medication cart 100. A user may log OFF manually or be automatically logged OFF in response to a predefined period of inactivity having lapsed. As another example, processor 200 can generate an available notification signal in response to determining that none of drawers, sensors, or other components are currently being used.

The available notification signal can facilitate the providing of power and/or information to a local usage indicator (such as usage indicator 116) and/or other type of local user interface (such as display screen 112) via output module 220. In this regard, output module 220 can receive the available notification signal generated by processor 200 and, in response, send power to a lighting device, such as, e.g., light 120 of usage indicator 116, thereby causing light 120 to illuminate. In some embodiments, the available notification signal can also cause an in-use indicator to be disabled (e.g., turned OFF). For example, light 118 of usage indicator 116 can be adapted to indicate when medication cart 100 is in-use and, in response to receiving the available notification signal, output module 220 can be configured to stop powering light 118 of usage indicator 116.

Processor 200 can also be configured to provide an in-use notification signal and/or available notification signal, and/or any other type of usage status signals to communications module 230. Communications module 230 can include hardware, software, and/or any other means for transmitting and/or receiving data, content or any other type of information from a network device, such as those discussed in reference to FIG. 3.

The usage status signals provided to module 230 can be the same as, similar to, or different than the usage status signals processor 200 provides to output module 220. For example, the usage status signals provided to communications module 230 may include more data than the usage status signals provided to output module 220. The additional data may help a remote device determine other information related to medication cart 100. For example, one or more of the usage status signals sent communications module 230 can also identify the type of medication storage device associated with medication cart 100, the location of medication cart 100, user identifying information associated with medication cart 100, device-specific identifying information (such as the name) of medication cart 100, how medication cart is being used (e.g., the type of medication being dispensed), remaining supplies, among other things.

In some embodiments, processor 200 is in communication with or includes memory 240, such as volatile and/or non-volatile memory that stores content, data and/or any other information. For example, memory 240 typically stores information generated by, transmitted from, and/or received by, computing device 110. Also for example, memory 240 typically stores software applications, instructions or the like for the processor to perform steps associated with operation of computing device 110 and, in accordance with some embodiments, other components of medication cart 100 and/or a remote device (discussed more in reference with, e.g., FIG. 4). For example, memory 240 may be a nontransitory storage medium that stores computer program code comprising instructions that processor 200 executes to perform the steps described above and below with regard to, e.g., FIGS. 4A, 4B and 5.

In addition to the components discussed above, processor 200 can also be connected to at least one user interface or other means for displaying usage status notifications data, content or other information to the user. For example, display module 250 may enable processor 200 to display information to the user via display screen 112. Among other things, display module 250 can cause display screen 112 to indicate the usage status of computing system 110 and/or medication cart 100.

Figure 3:
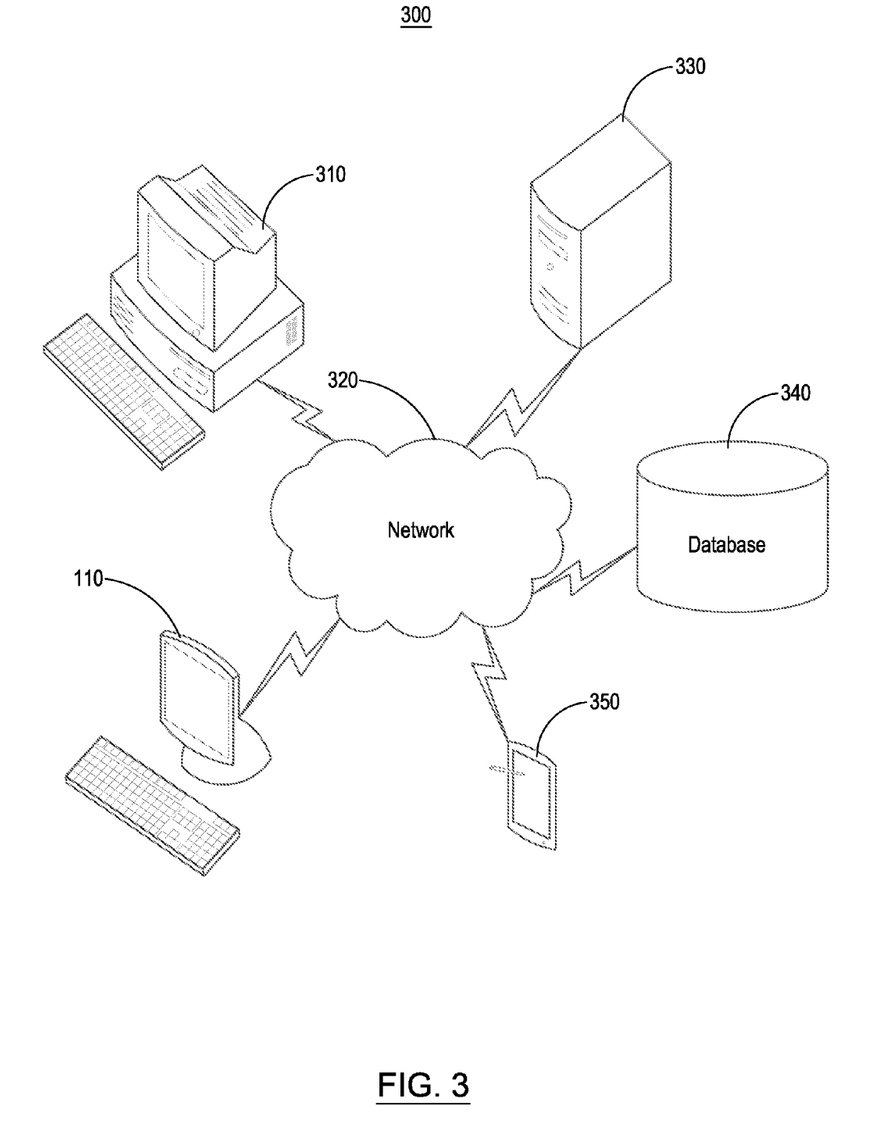
FIG. 3 is a system diagram capable of operating in accordance with some embodiments.

Referring to FIG. 3, system 300 is shown as an exemplary networked system that may benefit from embodiments provided herein. In addition to computing device 110, system 300 may further include central usage indicator 310, network 320, central server 330, database 340, and handheld usage indicator 350. System 300 can be associated with a healthcare department, healthcare facility and/or entire enterprise in which the computing device 110 and/or other types of medication storage devices are being used or available for use. Computing device 110 may use communications module 230 to access network 320 and the other devices attached thereto, including the central server 330, in order to provide and/or receive usage status signals as well as other types of signals (such as, e.g., request additional information regarding the medication being dispensed by the healthcare worker). Network 320 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.).

In response to receiving a usage status signal from computing device 110, central server 330 may process and/or provide the usage status signal to central usage indicator 310, database 340, handheld indicator 350, and/or any other networked devices (not shown). For example, database 340 may store information associated with a plurality of medication storage devices including, for example, device name, device location, types of medication being stored, remaining quantities of medication being stored, whether the device is in-use or available, user identifying information associated with the current user and/or previous user(s) of the device, error information (including, e.g., the type of error and the time the device went into the error state), and/or any other information related to one or more medication storage devices. In an alternative embodiment, some or all of the additional information associated with each of the medication storage devices may be stored in memory associated with each of the medication storage devices (e.g., computing device 110), which central server 330 and/or the other medication storage devices can be configured to access, thus eliminating the need for database 340.

Some or all of the information, including usage status information and error information, stored in a central posting board in database 340 and/or among the medication storage devices can be presented using central usage indicator 310. In this regard, central usage indicator 310 can access a central posting board using, for example, a web application and/or by any other means. The central posting board can indicate, for example, whether computing device 110 and/or other medication storage devices are in-use, available for use, unable to be used (e.g., in an error state and, if so, when the device entered the error state), and/or associated with any other status information. The central posting board can also associate the displayed status information with one or more specific devices. For example, a green visual indicator can be displayed next to the name(s) and/or location(s) of each available medication storage device(s), while a red indicator can be displayed next to the name(s) and/or location of each in-use and/or otherwise unavailable medication storage devices. In some embodiments, medication storage devices that are unavailable due to a fault or other technical error can be distinguished from medication storage devices that are unavailable due to being in-use and/or out of medication or other supplies. Handheld indicator 350 and/or any other type of device can also be configured to access the posting board and provide some or all of the usage and other information associated with one or more medical storage devices. Handheld indicator 350 may be a tablet device, personal digital assistant, cellular phone, any other type of mobile device, or combination thereof.

For example, a medication storage device may be located in an area that is not easily accessible, such as in an operating room where surgery is being performed. Despite being able to see the mobile medication storage device through a door's window, absent implementation of an embodiment discussed herein, a medical worker may be unable to determine whether the mobile medication storage device is currently being used without calling the operating room via telephone (and risk interrupting the surgery) or taking the time to sterilize to enter the room. As such, embodiments discussed herein may allow the medical worker to avoid interrupting the surgery or wasting time sterilizing, only to learn the mobile medication storage device is currently being used. Embodiments provided herein would allow the healthcare worker to determine whether the medication storage device is being used, experiencing an error, or needing supplies, by looking through the door's window to see the usage indicator and/or checking a posting board.

While a lack of supplies may cause a healthcare worker to try and find another medication storage device, a pharmacist may want to find those medication storage devices that need supplies to replenish them. Embodiments discussed herein can allow a pharmacist to more easily and efficiently determine which medication storage devices are low on supplies and available for replenishing. Additionally, embodiments discussed herein can indicate the location of those medication storage devices. In this manner, the pharmacist or other type of healthcare worker may not have to wander the hospital halls or telephone other healthcare workers to determine whether one or more medication storage devices are being used and/or available for replenishing. In some embodiments, the healthcare worker or other types of users can sort, filter and/or otherwise organize the medication storage devices included in the posting board, such that only medication storage devices having particular usage or other characteristics are displayed and/or displayed in a particular manner.

As yet another example, embodiments can assist personnel who service the medication storage devices and/or the computing devices incorporated therein. As mentioned above, usage status signals generated by each medication storage device can allow the service personnel to determine whether a medication storage device is experiencing technical or other issues. The usage status notification or other type of visual indicator can also be generated in response to determining the presence of a fault condition or other type of technical error. Because the medication storage device can indicate when it is experiencing a fault, healthcare workers would no longer have to move faulty medication storage devices or those suspected to be experiencing technical errors to a remote location to physically prevent their use until the technical issues are resolved.

Figure 4A:
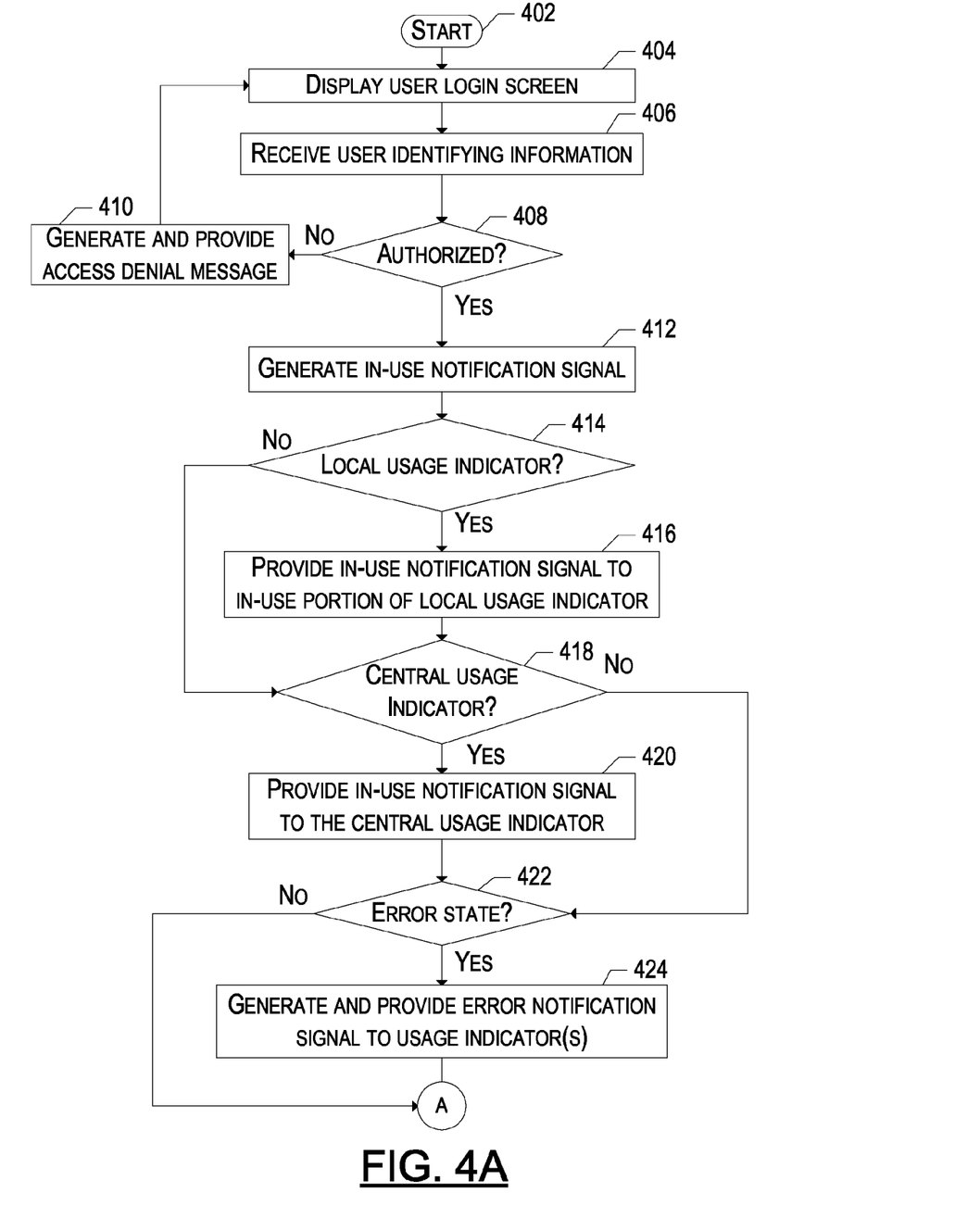
FIGS. 4A and 4B are flow charts showing an exemplary process for generating and providing usage status signals in accordance with some embodiments.
Figure 4B:
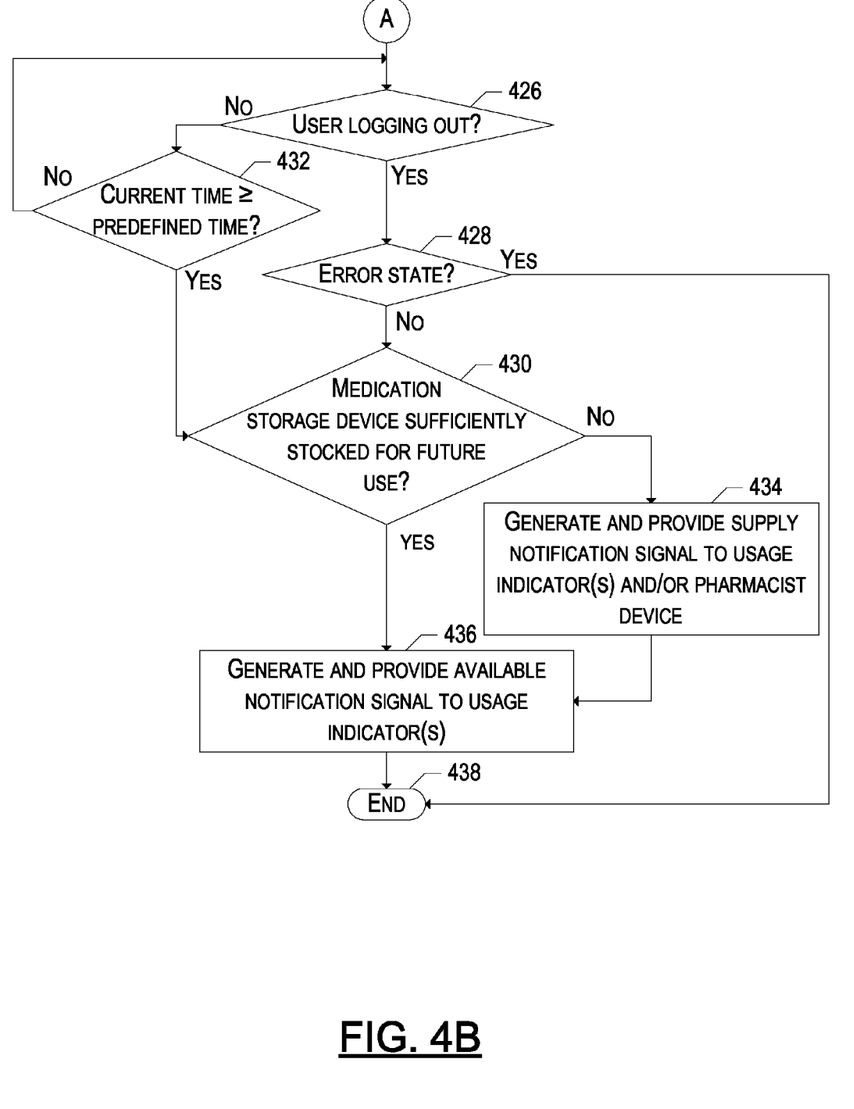
Figure 5:
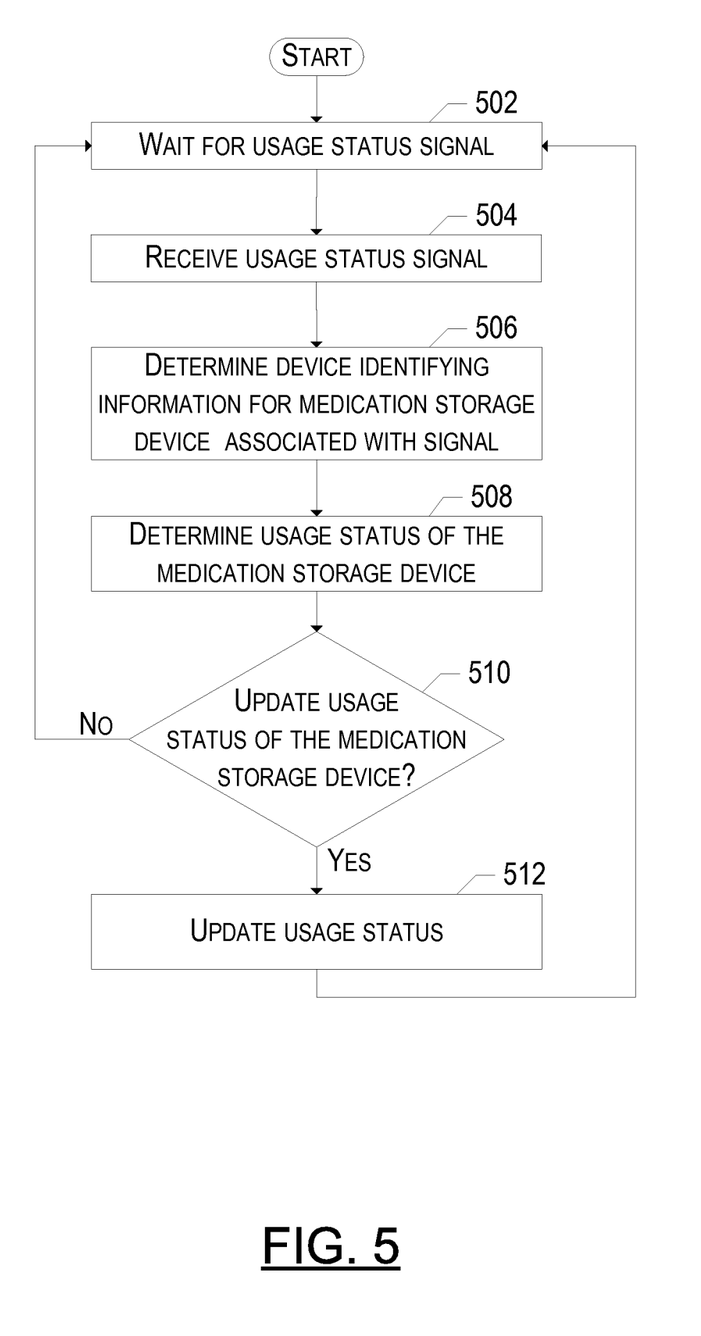
FIG. 5 is a flow chart showing an exemplary process of receiving and responding usage status signal with a remote device in accordance with some embodiments.

Referring now to FIGS. 4A, 4B and 5, operations are illustrated that may be taken to generate and send one or more usage status signals to one or more usage indicators in association with a medication storage device (e.g., a mobile medication dispensing cart, medication cabinet, nurse server, etc.) in accordance with some embodiments. For example, non-transitory computer readable media can be configured to store firmware, one or more application programs, and/or other software, which include instructions and other computer-readable program code portions that can be executed to control a medication storage device (e.g., processor 200), usage indicator, and/or network system to implement various operations, including the examples shown in FIGS. 4A-5. As such, a series of computer-readable program code portions are embodied in one or more computer program products and can be used, with a computing device, server, and/or other programmable apparatus, to produce a machine-implemented process.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein. In this regard, FIGS. 4A and 4B include process 400 which can be implemented on a medication storage device, such as the processor of medication cart 100, and/or a central device, such as server 330.

Process 400 starts at 402, which may occur when a healthcare worker (e.g., an anesthesia provider) comes into the healthcare facility in order to start his or her shift. At 404, a user login screen can be displayed by the processor upon the display of the medication storage device. The user login screen can prompt the user to enter user identifying information. For example, a user may be required to type a username, password, social security number, and/or any other information sufficient to verify the healthcare worker's identity. In some embodiments, entering user identifying information may also or instead comprise the user inserting a manual key into a lock, submitting to a biometric scan, presenting a RIFD card to a RFID reader, and/or performing any other action that enables the system to identify the user. At 406, the system, such as the processor, receives the user identifying information and determines whether to authorize access to the medication storage device. In response to determining the user is not authorized to access the medication storage device, an access denied message is generated and displayed at 410. In response to authenticating the user at 408, an in-use notification signal may be generated by the processor at 412.

In other embodiments, some examples of which are discussed above, the in-use notification signal may be generated in response to receiving a sensor output or other type of automatically generated signal that indicates the medication storage device is being used. For example, the in-use notification signal can be generated in response to receiving a signal indicating that a drawer has been opened, medication is being dispersed, or the like. In this regard, an automatically generated signal can be sufficient to cause the medication storage device to generate an in-use notification signal, even if a user has not logged into the system. In other embodiments, both an automatically generated signal and manually entered user identifying information may be required to generate an in-use notification signal at 412.

If the medication storage device includes a local usage indicator (such as usage indicator 116), process 400 can proceed to 416 and the in-use notification signal can cause the in-use portion of the local usage indicator to be activated (e.g., light 118 of usage indicator 116 can be turned ON). After 416 or if the medication storage device does not include a local usage indicator, process 400 can proceed to 418.

If the medication storage device is configured to communicate via a network with a central management system, process 400 can proceed to 420 and the processor can provide an in-use notification signal to a central usage indicator, such as a posting board application that can be accessed by any network device, including a handheld device, and/or one or more medication storage devices.

In some alternative embodiments, a network device, which may be located remotely from the medication storage device, can be configured to execute some or all of process 400 which is discussed above as being executed by the medication storage device. For example, a medication storage device can upload user identifying information received at 406, and upload the user identifying information to a central server that can determine at 408 whether or not the received user identifying information is authorized. In response to making an affirmative determination, the central server can remotely generate at 412 an in-use notification signal, which can be sent back to the medication storage device that received the user identifying information at 406. In some embodiments, whether the central server sends back the in-use notification signal can be dependent on a determination that the medication storage device includes a local usage indicator.

After 420 or if the medication storage device is not configured to access a central usage indicator, process 400 can proceed to 422. If an error state is detected or otherwise exists at 422, process 400 proceeds to 424 and the processor can generate an error notification signal that can be provided to a central and/or local usage indicator(s).

Process 400 continues in FIG. 4B. At 426, if the user is logging out or otherwise discontinuing use of the medication storage device (e.g., closing all open drawers, locking the medication storage device, etc.), process 400 proceeds to 428.

At 428, a determination is made as to whether an error state has been or is being detected by the medication storage device. For example, the determination can be based on whether there was error previously detected at 422 or whether a new error is being detected at the current time. In response to determining there is no error and/or was no error detected, process 400 continues to 430.

Process 400 will also continue to 430 subsequent to determining at 426 that the user is not logging out of the application and/or otherwise discontinuing the use of the medication storage device. Before proceeding to 430, the computing device (e.g., processor or similar means operating on computing device 110) may also have to determine at 432 whether the current time is equal to or greater than a predefined time. For example, the predefined time may be established by the user, or some other party (such as an information technology service provider) with access to the medication storage device and/or the software application operating on the medication storage device, as a time before which a majority of the cases or procedures being performed by the healthcare worker are likely to have been completed (and, therefore, the medication storage device should be locked). For example, the predefined time may correspond to 6:00 PM, or a time at which most operating rooms are closed.

At 430, a determination is made as to whether or not the medication storage cart is sufficiently supplied for future use. For example, the processor of the medication storage device can be configured to determine based on the remaining weight of a medication, the number of times a drawer was accessed, or by any other measurable variable associated with one or more supplies provided by the medication storage device.

In response to determining at 430 the medication storage device is not sufficiently stocked for future use, at 434 a supply notification signal, which is another exemplary type of usage status signal, can be generated by the processor of the medication storage device and/or a central device, such as server 330. The supply notification signal can then be provided to central and/or local usage indicators. In some embodiments, the medication storage device may be incorporated into a pharmaceutical and/or nursing automation system, such as McKesson's Connect-RX® integrated automation solution, which can be used to, e.g., indicate the usage status of one or more medication storage devices.

After 434 or in response to determining at 430 that the medication storage device is sufficiently supplied for future use, an application running on the medication storage device, such as being executed by the processor, and/or a central device can generate an available notification signal at 436, which can also be provided to the central and/or local usage indicator(s).

In addition to or instead of the medication storage device's processor determining it is available, a network device can be used to determine whether the medication storage device is or may be available. For example, a scheduling system may be referenced and/or used to generate an available notification signal based upon a predetermined schedule of procedures planned for the medication storage device. In this manner, the medication storage device may be scheduled to, for example, dispense anesthesia in an operating room from 10:00 am till 11:00 am, and after 11:00 am a determination can be made, using the scheduling information, that the medication storage device is available or is supposed to be available to receive supplies (or, e.g., available to be used). This type of availability information can then be provided to a pharmacist's system, the medication storage device, central device, and/or any other type of device and, when coupled with the supply notification signal generated at 434, can indicate the best time or times to replenish particular supplies of the medication storage device.

Process 400 can then end at 438 after generating an available notification signal and providing it to a usage indicator at 436. Process 400 will also end after 428 if an error state was detected at 422. One skilled in the art would appreciate that various steps discussed herein can be combined, omitted, and/or modified without departing from the spirit of the invention. For example, rather than being configured to generate four types of usage status signals, the medication storage device may be configured to generate only two (available and in-use).

With reference to FIG. 5, process 500 is shown as example of a machine-implemented method that can be implemented on a medication storage device, such as the processor of medication cart 100, and/or a central device, such as server 330.

Process 500 starts at 502, which may occur when a central device medication storage device, and/or any other type of network device is brought online. At 502, the device waits for a usage status signal. For example, a central device can wait for any type of usage status signal (including, e.g., an in-use, available, error, and/or supply notification signal). At 504, a usage status signal is received.

At 506, the received usage status signal is processed and the device identifying information is determined (e.g., extracted and/or parsed from) the usage status signal. In this manner, the name, location, and/or other information related to the medication storage device that generated or is otherwise associated with the usage status signal can be determined by the network device.

At 508, the usage status of the medication storage device is determined by the network device. For example, a determination can be made that the medication storage device is in-use, because a user is actively logged into an application executing on a computing device of the mediation storage device.

At 510, the network device can determine whether the usage status of the medication storage device can be uploaded to a database, provided to an application (such as a posting board) and/or provided to any other type of networked device, based upon, e.g., the usage status signal received at 504. For example, the medication storage device can remain in an in-use or other usage state until the user is logged OFF the application. While logged into the application, the medication storage device may generate one or more additional usage status signals when, for example, a drawer is opened, a technical error is being (or was) experienced, among other trigger events (some additional examples of which are discussed above). In response to receiving the usage status signal, the network device may or may not update the status of the medication storage device that is being presented by a usage indicator. In response to determining an update is unnecessary, process 500 returns to 502 and waits for another usage status signal. In response to determining an update is necessary, process 500 proceeds to 512 and a usage indicator or other type of user interface can be updated accordingly. For example, a display device can be updated to show the name, location and status of the medication storage device.

As described above and as will be appreciated by one skilled in the art, embodiments of the present invention may be configured as a method, medication storage device, central network device, and the like. Accordingly, embodiments may comprise various means including entirely of hardware or any combination of software and hardware. Furthermore, embodiments may take the form of a computer program product on at least one nontransitory computer-readable storage medium having computer-readable program instructions (e.g., computer software) embodied in the storage medium. Any suitable computer-readable storage medium may be utilized including hard disks, CD-ROMs, flash memory, optical storage devices, or magnetic storage devices.

Embodiments of the present invention have been described above with reference to block diagrams and flowchart illustrations of methods, apparatuses, systems and computer program products. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 200 discussed above with reference to FIG. 2, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 240) that can direct a computer or other programmable data processing apparatus (e.g., processor 200 of FIG. 2) to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for communicating a usage status of a medication storage device, wherein the medication storage device comprises at least one compartment configured to store medication and a display screen to present information to a user, the method comprising:
   receiving user identifying information;
   authenticating the user identifying information;
   in response to authenticating the user identifying information, logging a user into an application running on the medication storage device and determining the medication storage device is in-use;
   generating a usage status signal that corresponds with the medication storage device being in-use;
   indicating, using a usage indicator located local to the medication storage device, the medication storage device is in use based upon the usage status signal, wherein indicating the medication storage device is in-use occurs while the user is logged into the application; and
   indicating, using the display screen that is separate from the usage indicator, the medication storage device is in-use.

2. The method of claim 1 further comprising:
   determining the user is logged out of the application; and
   in response to determining the user is logged out of the application, indicating the medication storage device is available for use.

3. The method of claim 1, further comprising:
   determining the medication storage device is experiencing, a technical error state;
   generating an error notification signal; and
   indicating, using the usage indicator, the technical error state of the medication storage device.

4. The method of claim 1, further comprising:
   determining the medication storage device lacks sufficient supplies;
   generating a supply notification signal; and
   indicating, using the usage indicator, the medication storage device's lack of the sufficient supplies.

5. The method of claim 1 further comprising providing power to the usage indicator that is attached to the medication storage device to indicate the medication storage device is in-use.

6. The method of claim 1 further comprising sending an usage status signal to a remote usage indicator that is located remotely from the medication storage device.

7. The method of claim 6, wherein sending the usage status signal to the remote usage indicator further comprises sending data identifying the medication storage device and further comprising configuring the data to be displayed by an electronic poster board, wherein the electronic poster board is the remote usage indicator.

8. The method of claim 6, wherein sending the usage status signal to the remote usage indicator further comprises sending location data identifying a location of the medication storage device.

9. The method of claim 1, wherein indicating the medication storage device is in-use causes the usage indicator to disregard a previously sent usage status signal.

10. The method of claim 1 further comprising:
    determining a logout event has occurred; and
    in response to determining the logout event has occurred:
       generating an available notification signal; and
       sending the available notification signal to the usage indicator.

11. The method of claim 10, wherein determining the logout event has occurred is a result of determining the medication storage device has experienced a period of inactivity that is longer than a predetermined setting.

12. The method of claim 10, wherein determining the logout event has occurred is a result of a user logging out of an application running on the medication storage device.

13. A medication storage device, comprising:
    a display screen configured to present information to a user;
    at least one drawer configured to store medications;
    a usage indicator that is separate from the display screen; and
    a processor configured to:
       receive a signal indicating a user is logged in to an application running on the medication storage device;
       in response to receiving the signal:
          generate a usage status signal that corresponds with the usage status of the medication storage device;

provide the usage status signal to the usage indicator to indicate the medication storage device is in-use while the user is logged into the application; and cause the display screen to indicate the medication storage device is in-use while the user is logged into the application.

14. The medication storage device of claim 13, wherein the processor is further configured to cause the usage indicator to indicate the medication storage device is available in response to determining the user is logged out of the application.

15. The medication storage device of claim 13, wherein the processor is further configured to cause the usage indicator to indicate an error has occurred.

16. The medication storage device of claim 13, wherein the processor is further configured to cause the usage indicator to indicate supplies are needed for the medication storage device.

17. The medication storage device of claim 13, wherein the usage status signal includes power that illuminates at least a portion of the usage indicator.

18. The medication storage device of claim 13, wherein the medication storage device further comprises a communications module that is configured to facilitate communicating the usage status signal to a remote usage indicator.

19. The medication storage device of claim 13, wherein the usage indicator is positioned relative to the display screen to enable a line-of-sight for viewing the usage indicator from a distance farther than which the display screen is viewable when the user is standing in front of the display screen.

20. The medication storage device of claim 13 further comprising a vertical support member, wherein the usage indicator is affixed atop the vertical support member to enable a line-of-sight to the usage indicator from a distance.

21. A medication storage device, comprising:
a display screen configured to present information to a user;
at least one drawer configured to store medications;
a vertical support member;
a usage indicator that is separate from the display screen, wherein the usage indicator is affixed to the vertical support member to enable a line-of-sight to the usage indicator from a distance; and
a processor configured to:
cause the usage indicator to indicate a usage status selected from at least two different usage status options;
generate a usage status signal that corresponds with one of the usage status options, wherein the usage status options include an in-use status option, an available for use status option, a technical error status option, or a need for supply status option; and
provide the usage status signal to the usage indicator.

* * * * *